(12) United States Patent
Hauger et al.

(10) Patent No.: US 8,287,126 B2
(45) Date of Patent: Oct. 16, 2012

(54) SYSTEM AND METHOD FOR VISUALIZING OBJECTS

(75) Inventors: Christoph Hauger, Aalen (DE); Holger Matz, Unterschneidheim (DE); Marco Wilzbach, Stuttgart (DE)

(73) Assignee: Carl Zeiss Meditec AG, Jena (DE)

( * ) Notice: Subject to any disclaimer, the term of this patent is extended or adjusted under 35 U.S.C. 154(b) by 88 days.

(21) Appl. No.: 13/008,689

(22) Filed: Jan. 18, 2011

(65) Prior Publication Data
US 2012/0019777 A1 Jan. 26, 2012

Related U.S. Application Data

(60) Provisional application No. 61/295,376, filed on Jan. 15, 2010.

(51) Int. Cl.
*A61B 3/00* (2006.01)
*A61B 3/14* (2006.01)
(52) U.S. Cl. ......... 351/246; 351/206; 351/208; 351/210
(58) Field of Classification Search .................. 351/205, 351/206, 208, 209, 210, 246
See application file for complete search history.

(56) References Cited

U.S. PATENT DOCUMENTS

| | | | |
|---|---|---|---|
| 7,980,697 B2 * | 7/2011 | Tsukada et al. ............... | 351/208 |
| 2008/0084540 A1 | 4/2008 | Gaida | |
| 2009/0257065 A1 | 10/2009 | Hauger et al. | |
| 2010/0309478 A1 | 12/2010 | Reimer et al. | |

FOREIGN PATENT DOCUMENTS

| | | |
|---|---|---|
| DE | 10 2007 019680 A1 | 5/2008 |
| EP | 0 697 611 A2 | 2/1996 |

OTHER PUBLICATIONS

Do D. et al., "The impact of Optical Coherence Tomography on Surgical Decision Making in Epiretinal Membrane and Vitreomacular Traction", Trans Am Opthalmol Soc. 104:161-166, 2006.
Dr. Lumbroso B., "Image enhancement for clinical pre and post op assessment".

* cited by examiner

*Primary Examiner* — Jack Dinh
(74) *Attorney, Agent, or Firm* — Kilpatrick Townsend & Stockton LLP

(57) ABSTRACT

A method of visualizing objects using an optical system including an OCT system configured to obtain OCT data from voxels within a first volume having a first lateral extent includes obtaining position data indicative of a position of a predetermined portion of a movable instrument relative to the optical system and determining a first set of voxels from the voxels of the first volume based on the determined position such that at least 80% of the first set of voxels is located within a second volume having a second lateral extent with a size at least half the size of the first lateral extent. The method also includes obtaining OCT data of the first set of voxels, visualizing a representation of the OCT data of the first set of voxels, and repeating the steps of the method at a first repetition rate higher than 5 times per second.

28 Claims, 6 Drawing Sheets

SYSTEM AND METHOD FOR VISUALIZING OBJECTS

CROSS-REFERENCES TO RELATED APPLICATIONS

The present application claims benefit under 35 U.S.C. §119(e) of U.S. Provisional Patent Application No. 61/295,376, filed on Jan. 15, 2010, entitled "System and Method for Visualizing Objects," the disclosure of which is hereby incorporated by reference in its entirety for all purposes.

BACKGROUND OF THE INVENTION

The invention relates to a method of performing eye surgery using an optical coherence tomography (OCT) system and a movable surgical instrument.

The invention also relates to a system for performing optical coherence tomography (OCT) assisted eye surgery with a movable surgical instrument.

SUMMARY OF THE INVENTION

Epiretinal membrane, also known as macular pucker is a disease of the eye, which is caused in particular by changes in the vitreous humor. Shrinkage and forward movement of the vitreous may cause traction or pulling on the retina, which can result in microscopic damages to its inner surface. The retina then may initiate a healing response with mobilization and migration of cells found within the retina itself. These cells then spread outward along the surface of the retina. This thin layer of scar tissue is referred to as macular pucker or epiretinal membrane. It typically progresses slowly and affects central vision by causing blurring and distortion. In the eyes of some patients, the layer of the epiretinal membrane on the surface of the macula results in mechanical wrinkling and distortion of the retina, which may lead to decreased vision.

A common surgical technique for treatment of epiretinal membranes is vitreoretinal surgery. The surgery starts with a procedure known as vitrectomy, wherein the vitreous jell is removed from the center of the eye. Thereby, any vitreous attachment is removed from the central macular region. Then, specialized microsurgical instruments are used to gently peel and remove the scar tissue from the surface of the retina, relieving the traction and reducing the distortion to the retinal surface.

When peeling the epiretinal membrane, only subtle visible clues, if any, help the surgeon to determine the location of the border between the epiretinal membrane and the adjacent underlying retina. Also, it is difficult for the surgeon to determine the best edge of the epiretinal membrane for continuing the peeling process. In order to facilitate the procedure of membrane peeling, the epiretinal membrane is therefore typically stained using dyes such as indocyanine green or trypan blue.

However, said dyes raised questions with regards to their safety. Reports have been published, which discussed the possibility of toxicity of these dyes to the retinal cells.

Therefore, a need exists for facilitating and increasing the safety of surgeries for vitreoretinal diseases.

The present invention has been accomplished taking the above problems into consideration.

Embodiments of the present invention provide a method of visualizing objects using an optical system including an OCT system configured to obtain OCT data from voxels within a first volume having a first lateral extent, the method comprising: obtaining position data indicative of a position of a predetermined portion of a movable instrument relative to the optical system; determining a first set of voxels from the voxels of the first volume based on the determined position such that at least 80% of the first set of voxels is located within a second volume, the second volume having a second lateral extent, wherein the second lateral extent has a size which is at least 2 times smaller than a size of the first lateral extent; obtaining OCT data of the first set of voxels; visualizing a representation of the OCT data of the first set of voxels; and repeating the obtaining of the position data, the determining of the first set of voxels, the obtaining of the OCT data of the first set of voxels and the visualizing of the representation at a first repetition rate higher than 5 times per second.

The objects may comprise a portion of the anterior portion of the eye and/or a portion of the posterior portion of the eye. For example, the objects may comprise an epiretinal membrane and/or a layer of the retina.

The term lateral may be defined herein as being oriented perpendicular to the optical axis of the optical system, which directs the OCT beam of light toward the objects. For example the term lateral may be defined as being oriented perpendicular to the optical axis of the objective lens of the OCT system. In other words, the term lateral may be defined as being oriented perpendicular or substantially perpendicular to the direction of the OCT measuring beam in the object region.

Between the objective lens of the OCT system and the objects, the OCT measuring beam may pass further lens elements of the optical system, such as a contact ophthalmoscopy lens system or an ophthalmic magnifier lens.

The OCT system is configured to obtain OCT data from voxels within a first volume of the object. The term voxel may be defined herein as being a volume element in the object region of the OCT system, wherein a volumetric data point of the OCT system is assigned to said volume element. The first volume may be the scannable volume of the OCT system. In other words, the first volume may be defined as being the sum of the voxels of the first volume. The first volume may be defined as the volumetric portion, which is recordable by the OCT system.

The first volume has a first lateral extent having a size. The size of the first lateral extent may be defined as being the size of the area, which is obtained by projecting the voxels, i.e. the volume elements of the volumetric data points, of the first volume onto a laterally oriented plane.

Further according to the method, position data is obtained, which is indicative of a position of a predetermined portion of a movable instrument relative to the optical system. The movable instrument may be for example forceps, scissors, a scalpel and/or a needle. The predetermined portion of the instrument may be a distal portion of the instrument. For example, the predetermined portion may comprise the jaws of the forceps or the blade of the scalpel.

The position data may be obtained by the OCT system. For example, the position data may be obtained by scanning voxels of the first volume, which are located on the surface and/or within the volume of the instrument. For example, in case the instrument is made at least in part of a material, which is semitransparent or transparent to the OCT measuring beam, the OCT system may scan voxels within the volume of the instrument.

Additionally or alternatively, the position data may be obtained by a surgical microscope. For example, the surgical microscope may be configured to image a portion of the movable instrument. The position data, which are indicative of the predetermined portion of the movable instrument may be obtained by applying an image processing routine to the images of the imaged portion of the movable instrument. The predetermined portion may be different from, overlapping with or identical to the imaged portion.

Additionally or alternatively, the position data may be obtained by a manipulator, which controls the movements of the instrument. For example, the position data may be obtained from signals of the drive motors of the manipulator of the instrument and/or from sensors of the manipulator.

The position data may comprise coordinate values of a coordinate system, which is fixed in relation to the OCT system. The position data may comprise for example at least one of the following: x, y, z-coordinate values of a coordinate system, which is fixed in relation to the OCT system, an orientation angle $\phi$ of a longitudinal axis of the instrument with respect to the z-axis of the coordinate system, position of the instrument along the longitudinal axis of the instrument and rotation angle $\theta$ of the instrument around the longitudinal axis of the instrument. The position data may further comprise an opening angle of the jaws of the instrument.

A first set of voxels is determined depending on the determined position of the movable instrument. The first set of voxels is a subset of the voxels of the first volume.

At least 80% of the first set of voxels is located within a second volume, the second volume having a second lateral extent, wherein the second lateral extent has a size, which is at least 2 times smaller than the size of the first lateral extent of the first volume. The size of the first lateral extent and the size of the second lateral extent may be measured in square meters. For example, the second volume may be a sum of at least 80% of the voxels of the first set of voxels. In other words, at least one volume, which comprises 80% of the first set of voxels has a second lateral extent, wherein the second lateral extent of said volume has a size which is at least 2 times smaller than the size of the first lateral extent.

The size of the second lateral extent may be at least 10 times smaller than the size of the first lateral extent. Also, it is possible that the size of the second lateral extent is at least 100 times smaller than the size of the first lateral extent. Moreover, it is possible that the size of the second lateral extent is at least 1000 times smaller than the size of the first lateral extent.

The second lateral extent may be defined herein as the area, which is obtained by projecting the voxels of the second volume onto the laterally oriented plane (i.e. a plane, which is oriented perpendicular to a direction of the OCT measuring beam in the object region). The second volume may be defined as the sum of the at least 80% of the first set of voxels, which are located within the second volume. The laterally oriented plane for determining the second lateral extent may be the same laterally oriented plane as for determining the first lateral extent.

Determining the first set of voxels based on the determined position of the instrument may comprise choosing the first set of voxels such that the location of each voxel of the first set of voxels is moved depending on or in correspondence to the movement of the instrument. Accordingly, the second volume may be moved in correspondence with the movement of the instrument. For example, the location of the voxels of the first set of voxels may be translated in the same direction and by the same distance as the predetermined portion of the instrument. Furthermore, the location of the voxels of the first set of voxels may be rotated about the same axis and through the same angle as the predetermined portion of the instrument.

Determining the first set of voxels based on the determined position of the instrument may further comprise determining the location of the first set of voxels depending on an operation state of the instrument. For example, the first set of voxels may be determined depending on whether and to which extend the jaws of the forceps are opened. Thereby, a portion of the first set of voxels may for example comprise the space between the jaws of the forceps.

A percentage of less than 20% of the first set of voxels may be located outside the second volume. For example, said less than 20% of the first set of voxels may be located on the surface or within the volume of the instrument. For example, the second volume may be located outside the movable instrument and the less than 20% percent of the first set of voxels may be located on the surface or within the volume of the instrument. Thereby, position data indicative of a position of the predetermined portion of the instrument may be obtained from the OCT data of the first set of voxels.

Alternatively or additionally, the second volume may comprise a portion of the instrument.

OCT data of the first set of voxels are obtained. The OCT data of the first set of voxels may be obtained by scanning the first set of voxels with the measuring beam of the OCT system. The representation of the OCT data may be defined as a graphical illustration of the OCT data. The representation may comprise for example a curve and/or a three-dimensional illustration. Visualizing the representation may comprise showing the representation on a computer screen and/or printing the representation.

The obtaining of the position data, the determining of the first set of voxels, the obtaining of the OCT data of the first set of voxels and the visualizing of the representation may be performed, for example in that order, at a first repetition rate, which is higher than 5 times per second.

The first repetition rate may be higher than 10 times per second or higher than 20 times per second or higher than 50 times per second or higher than 100 times per second.

Accordingly, it is possible to obtain the OCT data of the first set of voxels at a first repetition rate, which is high compared to a repetition rate at which the first volume is scannable. Thereby, it is possible to continuously record changes of the objects, which are caused by the movement of the instrument in real-time. Furthermore, since the first set of voxels is based on the determined position of the movable instrument, the first set of voxels is determinable such that a portion of the first set of voxels is located within a portion of at least one of the objects, wherein said portion of the objects is expected to be modified and/or affected by the operation of the instrument. For example, the at least one portion of the first set of voxels may be located within the space between the jaws of the forceps or between the blades of the scissors. Accordingly, the portion of the object, which is expected to be modified or affected by the instrument is recorded at a high repetition rate. Thereby, the surgeon is able to observe in real-time, how the operation of the instrument affects the object. This allows the surgeon to perform surgical procedures with a high accuracy.

Accordingly, since the surgical operation can effectively be observed by using OCT, it is possible to perform vitreoretinal surgery without the need of staining the epiretinal membrane with potentially toxic dyes.

Additionally or alternatively, geometrical data representing the shape of a distal portion of the instrument may be obtained by imaging the distal portion with an ophthalmic surgical microscope. For example, images acquired by the ophthalmic surgical microscope may be analyzed by using an image processing routine for extracting the geometrical data. The image processing routine may for example be a pattern recognition routine or an edge detection routine.

According to an embodiment, at least 90% of the first set of voxels is located within the second volume or 100% of the first set of voxels is located within the second volume.

According to a further embodiment, a scanning time for scanning the first volume with the OCT system may be at least two times or at least 10 times or at least 100 times or at least 1000 times longer than a scanning time for scanning the first set of voxels with the OCT system.

According to a further embodiment, the obtaining of the position data comprises analyzing of the OCT data obtained from the first set of voxels, and determining the position data based on the analysis of the OCT data.

A portion of the first set of voxels may be located within or on the surface of the instrument. Said portion may be located inside and/or outside the second volume.

Accordingly, it is possible to determine the position of the instrument with a high precision and at a comparatively high first repetition rate. In particular, it is possible not only to locate a lateral position of the instrument, but also a position of the instrument along the z-axis (i.e. along the optical axis) with a high precision.

The obtaining of the position data may further comprise obtaining data representing a geometrical shape of said predetermined portion. For example, in case the first set of voxels comprises said predetermined portion at least in part, data representing the geometrical shape of the predetermined portion may be obtained by analyzing OCT data of the first set of voxels.

The data representing the geometrical shape may be compared with predetermined geometrical data of the distal portion of the instrument. The predetermined geometrical data may have been obtained for example through electron microscopy and/or light microscopy prior to the surgery. For example, said measurements with electron microscopy and/or light microscopy may yield the diameter and/or other geometrical data of the predetermined portion of the instrument. The predetermined geometrical data may be extracted from images of an electron microscope and/or light microscope by applying an image processing routine by using a computer. The image processing routine may be for example be a pattern recognition routine and/or an edge detection routine. Thereby, the extent and location of a displacement of the instrument can accurately and efficiently be calculated based on a comparison of the obtained geometrical shape with the predetermined geometrical parameter.

Accordingly, it is possible to accurately measure a displacement of the predetermined portion of the instrument which is caused by a movement of the instrument. Thereby, the location of the first set of voxels can be accurately determined.

According to an embodiment, the obtaining of the position data comprises obtaining OCT data from a second set of voxels located in a third volume. The voxels of the first volume comprise the second set of voxels. The second set of voxels are located in a third volume having a third lateral extent larger than the second lateral extent. The third lateral extent may be equal to or smaller than the first lateral extent. According to the embodiment, the obtaining of the position data further comprises determining the position data of the instrument depending on the analysis of the obtained OCT data from the second set of voxels.

According to an embodiment, the optical system further comprises an optical imaging system configured to image an object plane onto a detector, the detector carrying an array of pixels, and wherein the obtaining of the position data comprises obtaining intensity data from the array of pixels and determining the position data depending on an analysis of the intensity data.

Further according to an embodiment, the optical imaging system is a surgical microscope.

The optical imaging system may be designed such that it simultaneously images objects which are located at different locations in the object plane onto the detector. In other words, the optical imaging system may simultaneously image the object region at a predetermined magnification without the need of scanning a measuring beam.

Accordingly, by using the surgical microscope, it is possible to get positional data of the instrument without scanning a measuring beam of the OCT system. Thereby, it is possible to rapidly obtain the position data of the instrument, which results in a high first repetition rate.

According to an embodiment, the optical imaging system comprises an objective lens, wherein a beam path of the OCT system traverses the objective lens of the optical imaging system.

The objective lens of the optical imaging system may have a working distance of for example 200 mm. A beam combiner may direct the OCT beam path of the OCT system towards the objective lens. The beam combiner may be coated with a dichroic coating so that radiation from the OCT beam path is scannable continuously during a surgical operation simultaneously to the viewing of the objects by the optical imaging system.

Accordingly, a compact optical system is provided having a long working distance for both, the optical imaging system and the OCT system. Furthermore, the OCT system may output a location signal indicative of a location of the object to drive a motorized internal focusing lens of the optical imaging system. Thereby, the optical imaging system may be autofocused.

According to an embodiment, the OCT system comprises a beam scanner configured to direct an OCT measuring beam to different locations within the first volume.

The beam scanner may be designed such that the OCT measuring beam is scanned in a lateral direction. The OCT measuring beam, after having passed the beam scanner of the OCT system, may be directed by the beam combiner towards the objective lens.

According to a further embodiment, the OCT system is a Fourier domain OCT system.

According to a further embodiment, the OCT system is a time domain OCT system.

According to an embodiment, the method comprises: obtaining OCT data of a third set of voxels from voxels of the first volume; and visualizing a representation of the OCT data obtained from the third set of voxels.

For example, the third set of voxels may comprise the whole epiretinal membrane and portions of the underlying retina. The third set of voxels may be determined such that for each volume which is a sum of voxels representing at least 80%, of the voxels of the third set of voxels, the lateral extent of said volume exceeds the second lateral extent. Alternatively, the third set of voxels may be determined such that the sum of all voxels of the third set of voxels has a lateral extent which exceeds the second lateral extent. The lateral extent may be obtained by projecting the voxels of the respective volume onto the laterally oriented plane.

The lateral extent of each of said volumes has a size which may be at least 2 times, or at least 5 times, or at least 10 times, or at least 100 times or at least 1000 times greater than the second lateral extent.

According to an embodiment, the method further comprises visualizing a combined representation of the OCT data obtained by scanning the third set of voxels and the OCT data obtained by scanning the first set of voxels.

The combined representation may be a visualization of at least a portion of the objects, wherein the visualization is generated from data of the first set of voxels and from OCT data of the third set of voxels.

A combined representation may comprise for example three-dimensional models of and/or cross-sectional views through the objects generated from the OCT data. For example, the combined representation may comprise a segmentation of the complete epiretinal membrane.

According to an embodiment, the method further comprises repeating the obtaining of the OCT data from the third set of voxels at a second repetition rate less than the first repetition rate, and wherein the visualizing of the combined representation is repeated at a third repetition rate greater than the second repetition rate.

According to a further embodiment, the third repetition rate is equal to the first repetition rate. According to a further embodiment, the third repetition rate is equal to or less than the first repetition rate.

The third repetition rate may be the rate at which the combined representation is updated or brought in accordance with newly obtained OCT data from the first, the second and/or the third set of voxels.

Accordingly, OCT data, which is obtained at different repetition rates may be combined to form a combined representation. Thereby, it is possible to provide a visualization of a representation of the OCT data to the surgeon, wherein frequently changing portions of the object are updated at a high repetition rate and wherein less frequently changing portions of the object are updated at a lower repetition rate. Thereby, the available scanning performance of the OCT system is efficiently used to yield a more accurate visualization of the representation during a surgery. Thereby, the surgery can be performed with higher precision.

According to an embodiment the method further comprises identifying objects located within the first volume based on an analysis of the OCT data.

Further according to an embodiment, the method further comprises enhancing a visibility of selected ones of the identified objects.

The identified objects may comprise the epiretinal membrane and/or layers of the retina. The identification of the objects may for example be performed by pattern recognition and/or investigating the OCT data from voxels of various depths along the optical axis. For example, OCT data from voxels having the same lateral position but being located at different depths may be used to determine surfaces of objects and/or interfaces between the objects.

Illustrating the OCT data of voxels of the same lateral position but of different depths is commonly referred to as an A-scan. For example, an A-scan may be used to identify the epiretinal membrane and individual layers of the retina.

After objects have been identified, they may be selected to be displayed with an enhanced visibility. For example, the surgeon or the computer may choose the epiretinal membrane and specific layers of the retina to be displayed with enhanced visibility.

According to an embodiment, the enhancing of the visibility comprises displaying a first selected object with a first color and displaying a second selected object different from the first selected object with a second color different from the first color.

According to an embodiment, the enhancing of the visibility comprises displaying a surface of the selected object.

Examples for a surface of a selected object may be for example the surface of the epiretinal membrane and/or the surface of the underlying retina. Representations of the OCT data, which are unrelated to selected identified objects may be for example the space between the epiretinal membrane and the wrinkled retina.

Further according to an embodiment, the enhancing of the visibility comprises suppressing displaying of a portion of the representation of the OCT data of the first set of voxels which is unrelated to selected identified objects.

Additionally or alternatively, the enhancing of the visibility may comprise suppressing displaying of a portion of a representation of the OCT data of the first volume wherein the portion is unrelated to the selected identified objects.

Additionally or alternatively, the enhancing of the visibility may comprise suppressing displaying of a portion of the combined representation, wherein the portion is unrelated to the selected identified objects.

Enhancing of the visibility may further comprise displaying interfaces between layers of the retina.

According to an embodiment, the method further comprises determining a distance between a selected one of the identified objects and the movable instrument.

According to an embodiment, the method further comprises generating a signal if the determined distance is less than a predetermined threshold.

The distance between the instrument and a selected one of the identified objects is calculated for example based on the OCT data of the second set of voxels. The distance may also be calculated based on the predetermined geometrical data of the instrument. The predetermined geometrical data may be generated by measurements of the instrument prior to the surgery.

For example, a model of the jaws of forceps may be generated depending on images acquired by optical microscopy or electron microscopy. Based on said model which represents the predetermined geometrical data, it is possible to calculate the distance between the forceps and an underlying object from measurements of the position of the instrument.

Accordingly, it is possible to calculate the distance between the forceps and the objects, such as the epiretinal membrane, with high accuracy. Thereby, the epiretinal membrane or the retina is prevented from being injured by accidentally touching them with the instrument.

According to an embodiment, the identified objects comprise an epiretinal membrane.

According to a further embodiment, the method comprises visualizing a combined representation of data representing the movable instrument and one or a combination of the OCT data of the first set of voxels, the OCT data of the voxels of the first volume, the OCT data of the second set of voxels and the OCT data of the third set of voxels.

A representation of the movable instrument may comprise displaying lines, which show the contour of the instrument. The representation of the instrument may be marked with a color.

Accordingly, the surgeon may easily recognize the position of the instrument in the representation relative to the object. The surgeon thus may be able to accurately control the movement of the instrument.

According to a further embodiment, the method further comprises generating the data representing the movable instrument based on at least one of the position data indicative of the position of the movable instrument and predetermined geometrical data representing a shape of the movable instrument.

Further according to embodiments, an optical system comprises an OCT system and is configured to perform the method according to the embodiments.

Further according to an embodiment, the optical system further comprises a display, wherein the optical system is configured to visualize a representation of one or a combination of the OCT data of the first set of voxels, the OCT data of the voxels of the first volume, the OCT data of the second set of voxels and the OCT data of the third set of voxels and/or the combined representation.

According to a further embodiment, the display comprises at least one of the following: a pair of oculars, a head mounted display, a head mounted display and a 3D monitor.

According to an embodiment, the movable instrument includes forceps.

Further according to an embodiment, the movable instrument comprises at least one reflecting component.

The reflecting component may comprise a retroreflector, which is designed such that the OCT measuring beam, when incident on the retroreflector, is retroreflected. The system may be designed such that a position of the retroreflector can be determined from the retroreflected OCT measuring beam.

Alternatively or additionally, the instrument may comprise nanoparticles, wherein the nanoparticles are detectable by the OCT measuring beam and wherein the system is designed such that the position data of the instrument can be obtained from the OCT light reflected from the nanoparticles.

Accordingly, it is possible to obtain position data indicative of a position of a predetermined portion of the movable instrument with a high accuracy.

BRIEF DESCRIPTION OF THE DRAWINGS

The foregoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

DETAILED DESCRIPTION OF THE INVENTION

Figure 1:
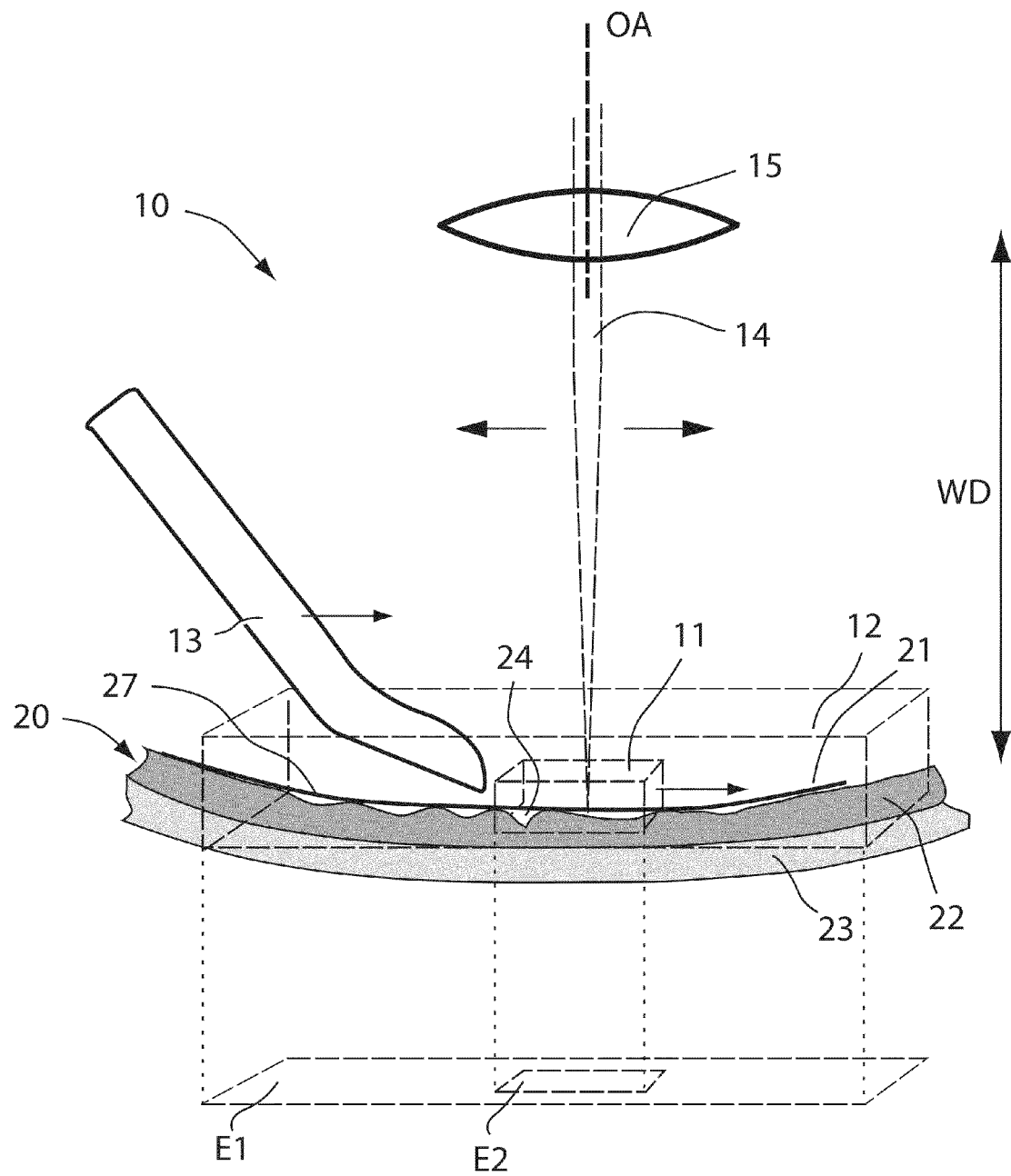
FIG. 1 schematically illustrates a method for performing surgery on the retina of the eye according to an embodiment.

FIG. 1 schematically illustrates the method according to an embodiment. The optical system 10 comprises an objective lens 15 and a movable instrument 13. The movable instrument 13 may be for example forceps, scissors, a scalpel and/or a needle. The objective lens 15 focuses an OCT measuring beam 14 on the objects. Between the objective lens 15 and the objects, the OCT measuring beam 14 may further pass a contact ophthalmoscopy lens system 16 and the lens of the eye 2000 (not shown in FIG. 1). The optical system, which directs the OCT measuring beam has an optical axis OA, which is defined by the objective lens 15. The objects in this case are portions of the posterior portion of the eye 20, which comprises the epiretinal membrane 21, the retina 22 and the choroid 23. The movable surgical instrument 13 in this case is designed such as to allow the surgeon to peel off the epiretinal membrane 21 from the retina 22. The objective lens 15 is located at a working distance WD of approximately 200 mm away from the posterior portion of the eye 20.

The optical system 10 is configured to obtain OCT data from voxels within a first volume 12. The first volume 12 may be defined as being all voxels, which are measureable by the OCT system. In other words, the first volume may be defined as the scannable volume of the OCT system.

The first volume 12 comprises the epiretinal membrane 21, such that the optical system 10 can take OCT data from the epiretinal membrane 21 and later provide a segmentation of the complete epiretinal membrane 21 to the surgeon. The first volume 12 further comprises portions of the underlying retina 22, such that the surgeon can identify from the OCT data of the first volume 12, non-attached portions 27 of the epiretinal membrane 21, where the epiretinal membrane 21 is not attached to the retina 22.

The first volume 12 has a first lateral extent El. The first lateral extent El may be defined as the area of the projection of the voxels of the first volume 12 on a lateral plane, which is oriented perpendicular to the optical axis OA of the OCT system.

Position data of the instrument 13 is obtained, which is indicative of a position of a predetermined portion of the movable instrument 13. The position data may be obtained in particular by the use of an ophthalmic surgical microscope (100 in FIG. 5) and/or by the OCT system.

A first set of voxels is determined based on the determined position of the instrument 13 such that at least 80% of the first set of voxels is located within a second volume 11.

The second volume 11 has a second lateral extent E2. The second lateral extent E2 may be defined as the area of the projection of the second volume 11 on the lateral plane, which is oriented perpendicular to the optical axis OA.

The second lateral extent E2 has a size which is at least 2 times smaller than the size of the first lateral extent E1. In other words, the size of the area representing the second lateral extent E2 is at least 2 times smaller than the size of the area representing the first lateral extent E1.

It is also possible that the size of the second lateral extent E2 is at least 10 times or at least 100 smaller than the size of the first lateral extent E1. The size of the second lateral extent E2 may even be at least 1000 times smaller than the size of the first lateral extent E1.

The first set of voxels is determined based on the position data of the movable instrument. By way of example, the first set of voxels—and thus the second volume 11—may perform a translational movement to the same extent as the instrument 13.

Since the size of the second lateral extent E2 of the second volume 11 is at least 2 times smaller than the size of the first lateral extent E1 of the first volume 12, the scanning time of the first set of voxels may be considerably shorter than the scanning time of the first volume 11. Thereby, it is possible to image a portion of the objects, which is expected to be modified or affected by the instrument 13, at a high repetition rate. Thereby, real-time data of the objects are obtainable and can be presented to the surgeon at a time-scale, which corresponds to the movement of the instrument 13. Thereby, the surgeon is able to perform the surgical operation with high accuracy.

Figure 2:
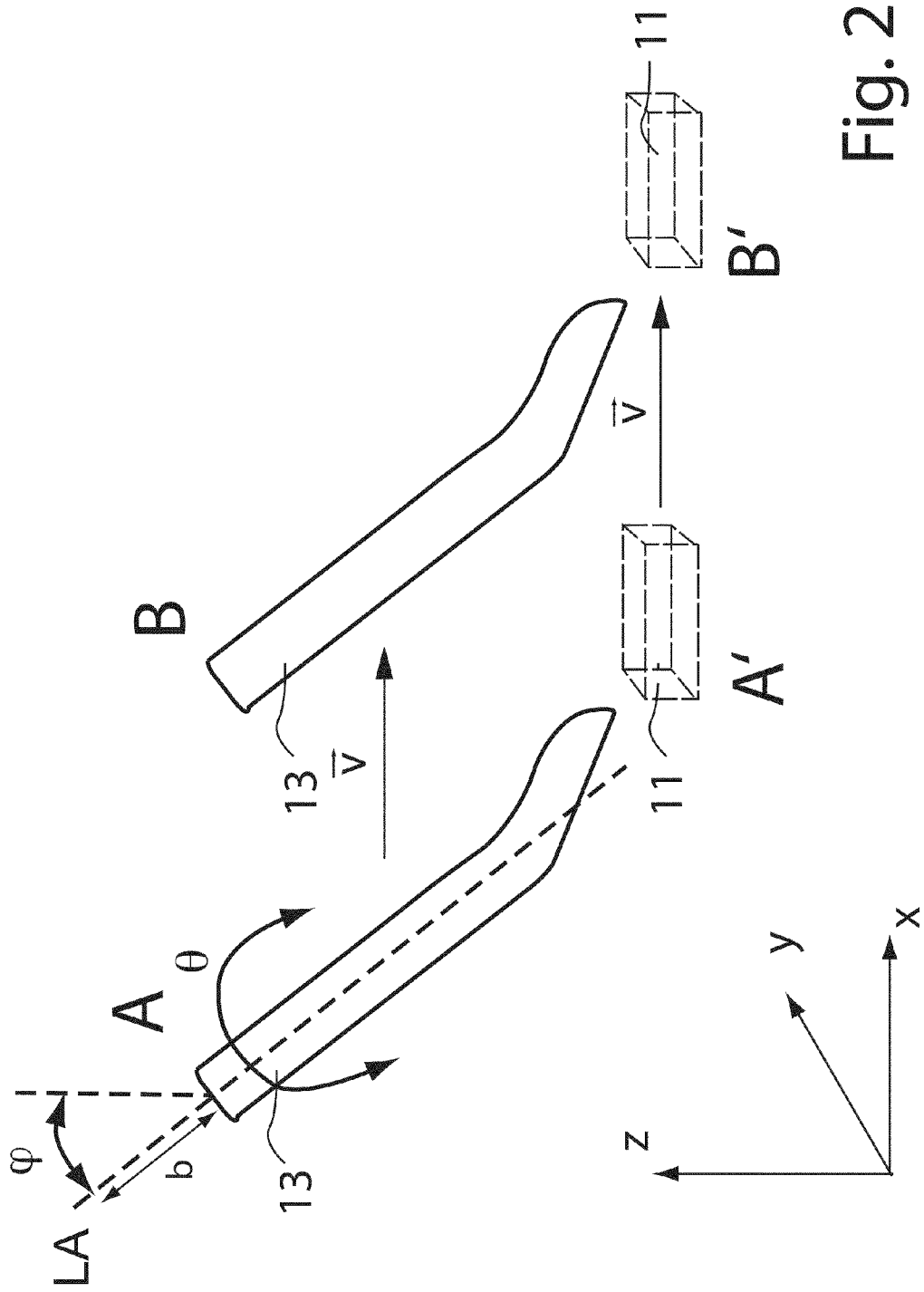
FIG. 2 schematically illustrates obtaining position data indicative of a position of a predetermined portion of the movable instrument and determining the first set of voxels based on the position data.

FIG. 2 schematically illustrates position data indicative of a position of a predetermined portion of the movable instrument 13 and the second volume 11 being determined based on the determined position of the instrument 13. The position data for example comprise an x-position, an y-position and a z-position in a coordinate system. The coordinate system is fixed in relation to the OCT system. The position data further comprise for example an inclination angle φ of a longitudinal axis LA of the instrument 13 with respect to the z-axis of the coordinate system, a rotational angle θ of the instrument around the longitudinal axis LA of the instrument 13 and a position b of the instrument 13 along the longitudinal axis of the instrument 13. Furthermore, the position data may also comprise the operation mode of the instrument 13. For example, in case of the instrument 13 comprises forceps, the operation mode may indicate whether and to which extent the jaws of the forceps are open or whether the jaws are closed.

The location and extent of the second volume 11 is determined based on the determined position of the instrument 13. FIG. 2 shows in an exemplary way, how the location of the first set of voxels may be determined based on the position of the instrument 13. When the instrument 13 moves from a position A to a position B by a translational movement, given by a translational vector $\vec{v}$, the first set of voxels, indicated by the second volume 11 may also perform a translational movement from position A' to position B' in the same direction and with the same distance, hence, described by the same translational vector $\vec{v}$.

The location of the first set of voxels may also be determined by a more complex mathematical dependence on the translational vector $\vec{v}$ of the instrument 13. Additionally or alternatively, the location of the first set of voxels may depend on at least one of the following: (a) the absolute values of the position data of the instrument 13, (b) the deviation of the position data with time (in other words, the velocity of the instrument 13), and/or (c) a value depending on the integration of the position data of the instrument 13 with time.

Additionally, the location of the first set of voxels may depend on the position of at least a portion of the objects, for example the position of the retina 22 and/or the epiretinal membrane 21. For example, location of the first set of voxels may be adapted to cover the line of the shortest distance between the epiretinal membrane 21 and the instrument 13. In other words, the position data of the instrument 13 may also comprise position data of the instrument measured relative to the position of at least a portion of the objects.

Additionally or alternatively, the location of the first set of voxels may depend on an operation mode of the instrument 13. For example, the location of the first set of voxels may be determined such that it comprises the region between the jaws of the forceps.

Accordingly, the first set of voxels may be determined such that it comprises a portion of the objects, which is expected to be modified or affected by the movement or operation of the movable instrument 13.

Figure 3:
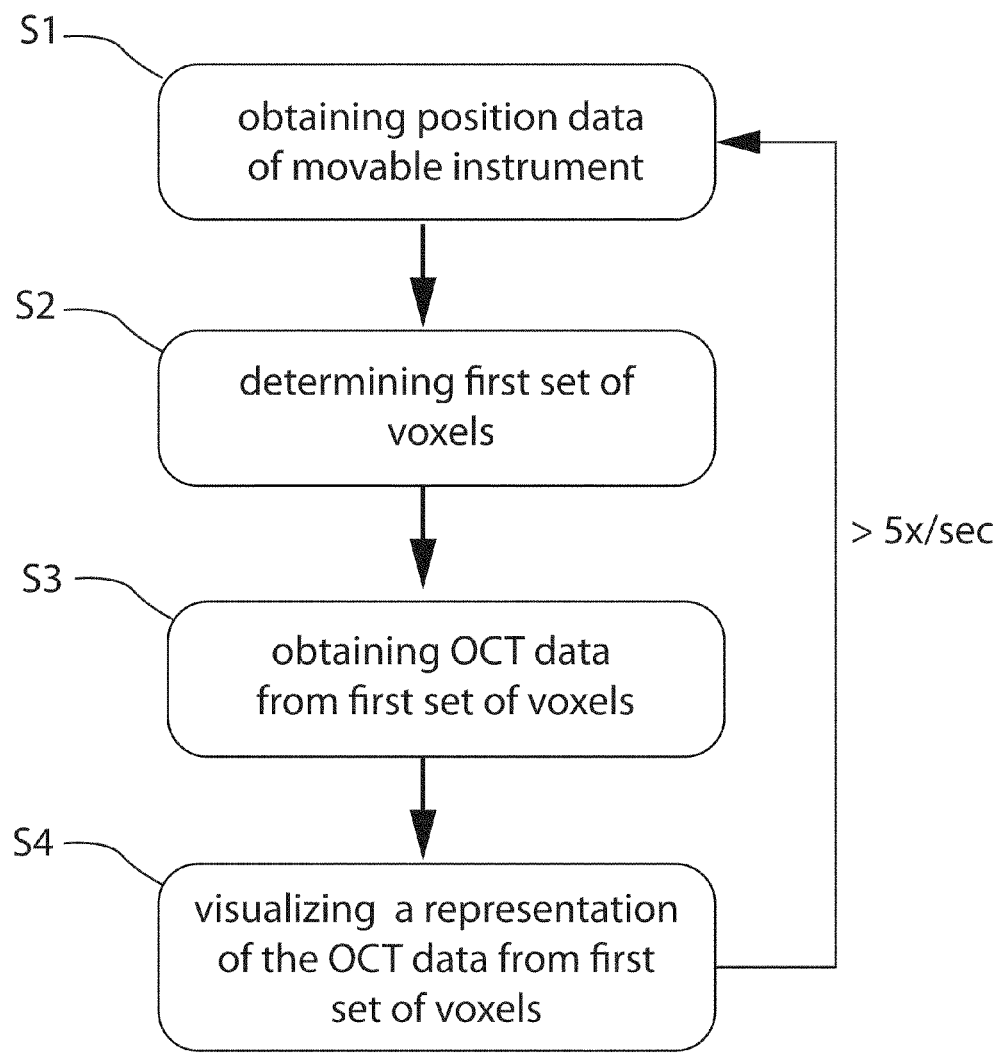
FIG. 3 illustrates a flow diagram according to an embodiment.

FIG. 3 illustrates a flow diagram according to an embodiment. Position data, indicative of the position of the movable instrument 13 are obtained S1. Then, the first set of voxels is determined based on the determined position S2. Afterwards, OCT data is obtained from the first set of voxels S3. Then, a representation of the OCT data from the first set of voxels is visualized S4.

The obtaining S1 of the position data, the determining S2 of the second volume 11, the obtaining of OCT data from the first set of voxels S3 and the visualizing of a representation of the OCT data from the first set of voxels S4 is repeated at a first repetition rate, which is higher than 5 times per second. The first repetition rate may even be higher. For example, the repetition rate may reach rates of 100 times per second or even higher.

The location of the first set of voxels may change between iterations, depending on the movement of the instrument 13 and further depending on how the first set of voxels is determined based on the determined position of the movable instrument 13.

Accordingly, the visualization of the representation of the OCT data obtained from the first set of voxels can be performed at a high rate, providing the surgeon with real-time information on those portions of the objects, which are expected to be modified or affected by the operation of the instrument 13.

Figure 4:
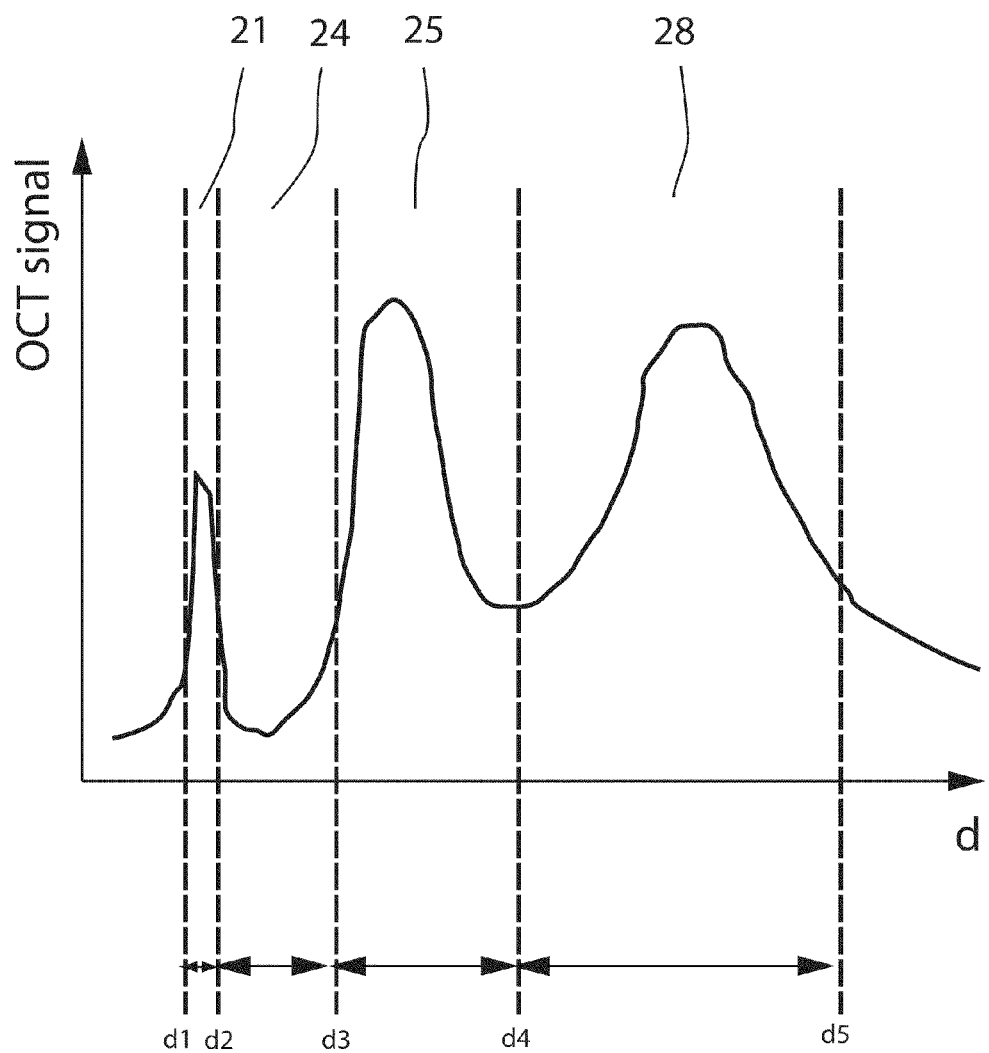
FIG. 4 illustrates a diagram of the OCT signal of voxels having the same lateral location and which are located at different depths (A-scan); retrieved by a method according to an embodiment.

FIG. 4 illustrates a diagram of OCT data taken from voxels of different depths, wherein said voxels are located at the same lateral position. Such a scan is commonly referred to as an A-Scan. The OCT signal, which represents the OCT data, is a measure of the intensity of scattered light at a voxel located at a certain depth d. From the OCT data, the location of objects of the posterior portion of the eye 20 can be identified. For example, from the data shown in the diagram of FIG. 4, an epiretinal membrane 21 can be identified ranging from a depth d1 to a depth d2, wherein the outer surface of the epiretinal membrane 26 is located at d1. From d2 to d3, there is a space 24 between the epiretinal membrane and the retina 21, indicating that the epiretinal membrane is not attached to the retina at that location. Furthermore, from the OCT data, a first layer of the retina 25 can be identified, ranging from d3 to d4 and a second layer of the retina 28 can be identified, ranging from d4 to d5.

Figure 5:
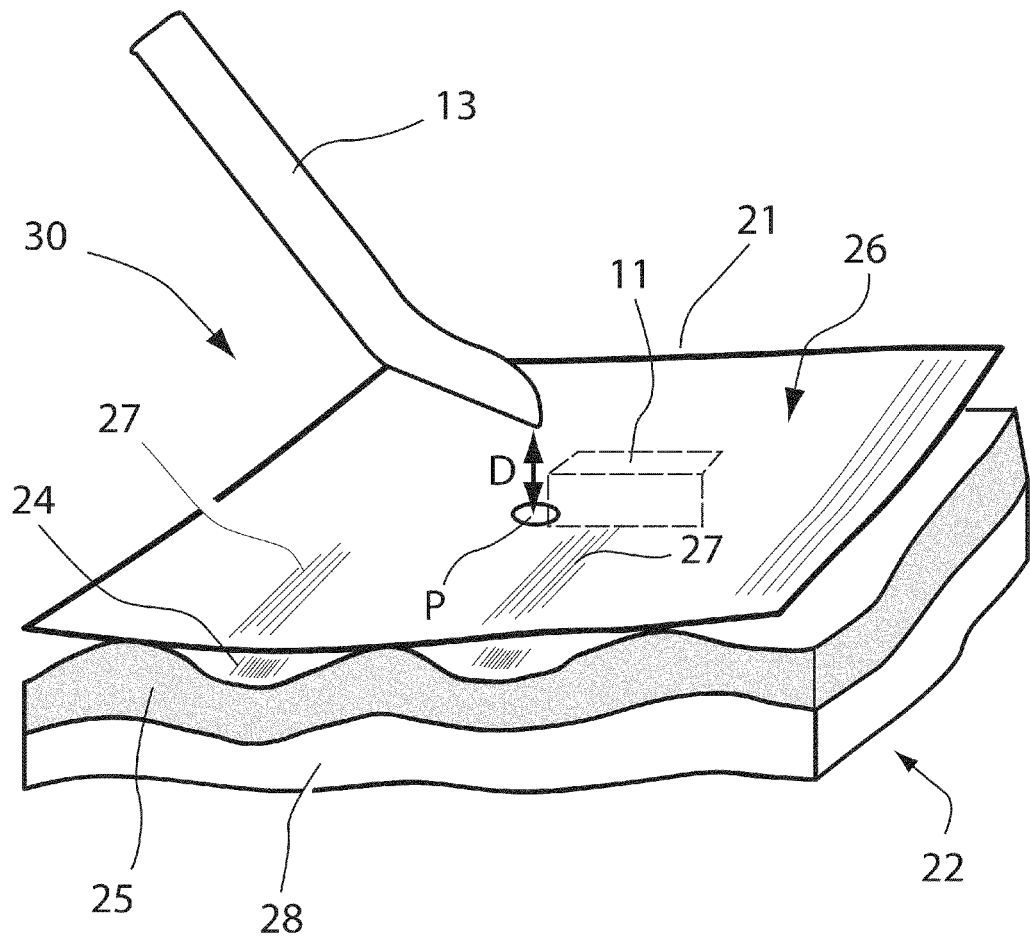
FIG. 5 illustrates a combined representation of objects identified from OCT data according to an embodiment.

The identified objects are visualized in a representation 30 of the objects, as illustrated in FIG. 5. In the representation 30, the visibility of selected objects is enhanced by displaying the objects with color and by marking surfaces and interfaces of the objects with lines. For example, the interface between the first layer of the retina 25 and the second layer of the retina 28 is indicated with a line. Furthermore, the peripheral of the epiretinal membrane is shown as a surface 26.

Through the representation 30 of the objects, the OCT data are easier to interpret for the surgeon during a surgical operation.

Also, in the representation 30, the surface 26 of the epiretinal membrane 21 is marked by dark regions 27 at locations, where the epiretinal membrane 21 is not attached to the retina 22, and where thereby is a space 24 between the epiretinal membrane 21 and the retina 21. Thereby, the surgeon is able to see the regions of the epiretinal membrane 21, which are not attached to the underlying retina 22.

Furthermore, it is possible for the surgeon to choose the location at the epiretinal membrane 21, where to start and/or continue the peeling process by moving the instrument 13.

The representation 30 further comprises a representation of the instrument 13. The representation of the instrument 13 is generated from the obtained position data and from a three-dimensional model of the instrument 13, hence from predetermined data of the instrument 13. The three-dimensional model has been generated by using electron microscopy and/ or light microscopy. Alternatively, it is possible to use a simplified model, comprising only a coarse contour of the instrument 13.

The representation 30 further displays the location and length of the closest distance D between the instrument 13 and the surface 26 of the epiretinal membrane 21. The representation 30 also shows the point P on the epiretinal membrane 21, from which the closest distance D is measured. The closest distance D is calculated based on the model of the instrument 13 and the determined position of a predetermined portion of the instrument 13. The predetermined portion in this case comprise the jaws of the forceps. In case the distance D is lower than a predetermined threshold, a signal is generated. Thereby, the surgeon is alerted.

Furthermore, since the distance D and the point P on the epiretinal membrane 21 are displayed in the representation and further since the regions 27 are shown, which indicate the portions of the epiretinal membrane 21, where the epiretinal membrane 21 is not attached to the underlying retina 22, the surgeon can accurately decide, where to start or to continue the process of epiretinal membrane peeling and further can accurately move the instrument 13 to said location.

Figure 6:
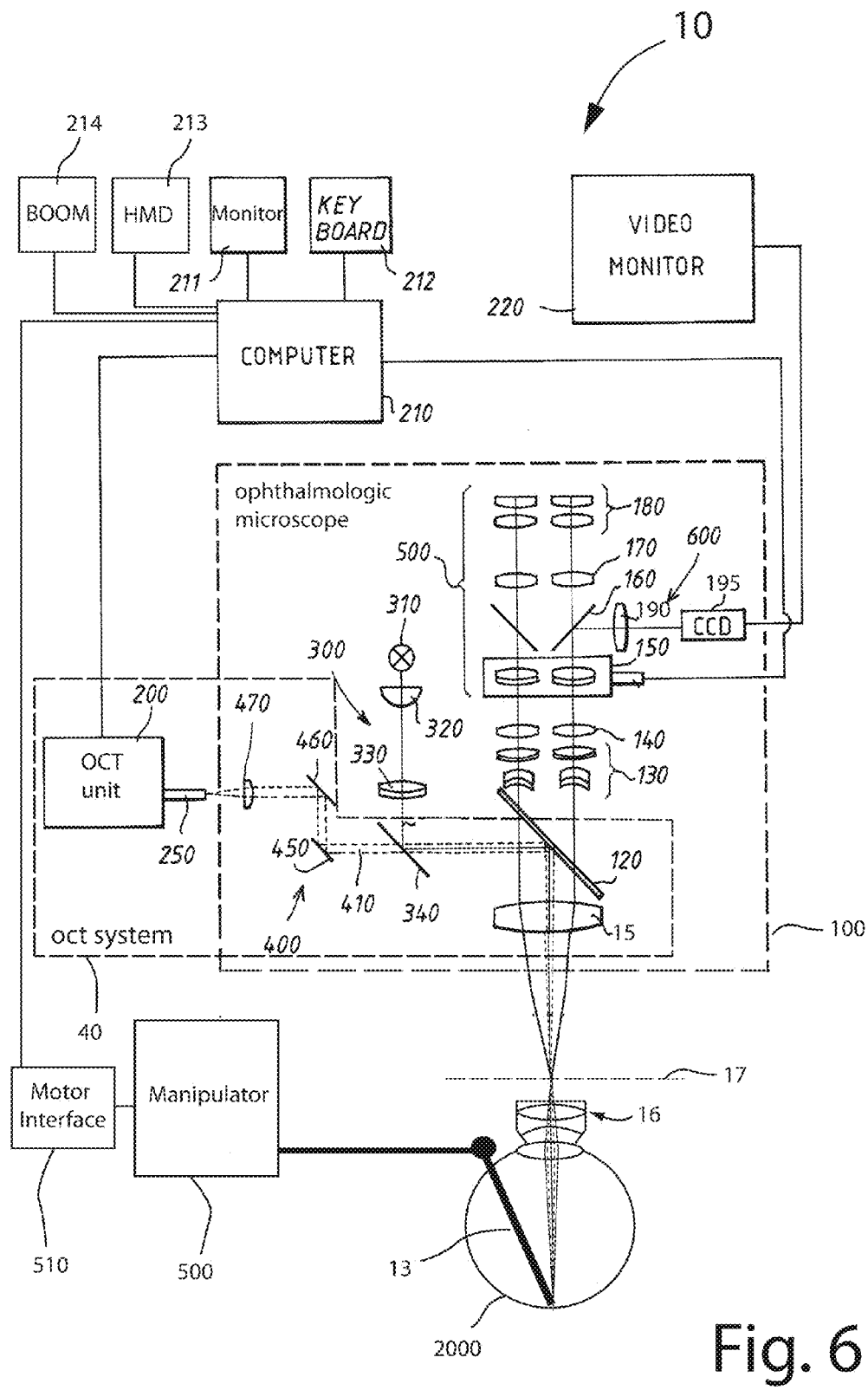
FIG. 6 schematically illustrates an apparatus for performing eye surgeries according to an embodiment.

FIG. 6 schematically illustrates the system for performing eye surgeries according to an embodiment. The system 10 comprises an OCT unit 200, which is a part of the OCT system 40. The OCT unit 200 comprises a CW radiation source, for example, a superluminescent laser diode having an output centered substantially at 850 nm. The output from OCT unit 200 over fiber 250 is coupled into OCT path 400. The OCT path 400 includes a beam scanner, which comprises two scanning mirrors 450, 460, which are orthogonally mounted and galvanometer driven. A lens 470 collimates radiation output from fiber 250. A beam combiner 120 directs the OCT radiation 410 from the OCT path 400 toward the objective lens 110 of the ophthalmic surgical microscope 100.

As shown in FIG. 6, the ophthalmic surgical microscope 100 further comprises, an optical magnification changer 130, which is set to a condition suitable for performing a particular surgical procedure. Typically there are a set of groups of lenses arranged on a drum for providing varying magnifications such as, for example, 5×, 12×, 20×, and so forth. Radiation impinging upon optical magnification changer 130 is collimated.

The optical system 10 further comprises a contact ophthalmoscopy lens system 16. The contact ophthalmoscopy lens system 16 may comprise one or more lens elements. One of said lens elements is configured such that it is arrangeable on the cornea of the eye 13. The contact ophthalmoscopy lens system images the ocular fundus of the eye 13 into an intermediate image plane 17 on which the viewing beam paths of the surgical microscope 100 are focused.

Instead of a contact ophthalmoscopy lens system 16, the optical system may comprise an ophthalmic magnifier lens and the surgical microscope may be provided with a reducing lens. The ophthalmoscopic magnifier lens may be configured such that it images the fundus of the eye 13 into an intermediate image plane 17 on which the viewing paths of the surgical microscope 100 are focused. The reducing lens may be arranged between the ophthalmic magnifier lens and the objective lens. An example for an optical system, which comprises an ophthalmic magnifier lens and a reducing lens is disclosed in document US 2008/0084540 A1, the content of which is incorporated herein as reference.

Ophthalmic surgical microscope 100 further comprises: (a) relay lenses 140, which take collimated output from optical magnification changer 130 and form an intermediate image of an object, for example eye 2000; and (b) internal focusing lenses 150, which are used to focus on the intermediate image of the object formed by relay lenses 140 and provide a collimated beam. Internal focusing lenses 150 move up and down along viewing path 500 to provide an opportunity for internal focus adjustment.

Additionally or alternatively to the relay lenses 140 and/or the focusing lenses 150, the ophthalmic surgical microscope 100 may be provided with a drive which is configured such that the ophthalmic surgical microscope 100 is movable such that its viewing beam paths are focused on the intermediate image plane 17.

After passing through internal focusing lenses 150, radiation is collimated and beamsplitter 160 couples a portion of the collimated radiation into optical path 600 for obtaining a video image. The video image is obtained by use of video lens 190, CCD camera 195, and video monitor 220.

Lastly, tube lenses 170 focus collimated radiation passed through beamsplitters 160 at an object plane of eye pieces 180. Eye pieces 180 then provide collimated output which is focused by a viewer's eyes. Since the above-described viewing path 500 is binocular, stereoscopic viewing can be obtained.

As further shown in FIG. 6, illumination path 300 is comprised of: (a) incandescent light source 310; (b) condenser lens 320 for collecting radiation output from light source 310; and (c) image lens 330 for filling the entrance pupil of objective lens 110 with the filament of incandescent light source 310. Beam combiner 340 combines OCT beam 410 with illumination radiation 310 from illumination path 300.

The movement of the instrument 13 is carried out by a manipulator apparatus 500. The manipulator apparatus 500 comprises drive motors, which are connected to a computer system via a motor interface 510.

The manipulator apparatus 500 may comprise sensors, which are designed to additionally or alternatively obtain positional data of the instrument 13.

The optical system 10 further comprises a display for displaying the OCT data and/or the representation 30 of the OCT data. The display may comprise a monitor 211, which may in particular be a 3D monitor. Additionally or alternatively, the display may comprise a head-mounted display 213 and/or a BOOM system 214 for recording motions of the surgeon. The motions of the surgeon may be recorded by means of data gloves and/or a 3D mouse.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. A method of visualizing objects using an optical system including an OCT system configured to obtain OCT data from voxels within a first volume having a first lateral extent, the method comprising:

obtaining position data indicative of a position of a predetermined portion of a movable instrument relative to the optical system;

determining a first set of voxels from the voxels of the first volume based on the determined position such that at least 80% of the first set of voxels is located within a second volume, the second volume having a second lateral extent, wherein the second lateral extent has a size which is at least 2 times smaller than a size of the first lateral extent;

obtaining OCT data of the first set of voxels;

visualizing a representation of the OCT data of the first set of voxels; and repeating the obtaining of the position data, the determining of the first set of voxels, the obtaining of the OCT data of the first set of voxels and the visualizing of the representation at a first repetition rate higher than 5 times per second.

2. The method according to claim 1 wherein the obtaining of the position data comprises analyzing of the OCT data of the first set of voxels, and determining the position data based on the analysis of the OCT data of the first set of voxels.

3. The method according to claim 1 wherein the obtaining of the position data comprises obtaining OCT data of a second set of voxels from voxels within the first volume and located in a third volume having a third lateral extent larger than the second lateral extent, and determining the position data based on an analysis of the obtained OCT data of the second set of voxels.

4. The method according to claim 1 wherein the optical system further comprises an optical imaging system configured to image an object plane onto a detector, the detector carrying an array of pixels, and wherein the obtaining of the position data comprises obtaining intensity data from the array of pixels, and determining the position data based on an analysis of the intensity data.

5. The method according to claim 4 wherein the optical imaging system is a surgical microscope.

6. The method according to claim 4 wherein the optical imaging system comprises an objective lens, wherein a beam path of the OCT system traverses the objective lens.

7. The method according to claim 1 wherein the OCT system comprises a beam scanner configured to direct an OCT measuring beam to different locations within the first volume.

8. The method according to claim 1 wherein the OCT system comprises a Fourier domain OCT system.

9. The method according to claim 1 wherein the OCT system comprises a time domain OCT system.

10. The method according to claim 1 further comprising;
obtaining OCT data of a third set of voxels from the voxels of the first volume;
visualizing a representation of the OCT data of the third set of voxels.

11. The method according to claim 10 further comprising visualizing a combined representation of the OCT data of the third set of voxels and the OCT data of the first set of voxels.

12. The method according to claim 11 further comprising repeating the obtaining of the OCT data of the third set of voxels at a second repetition rate less than the first repetition rate, and wherein the visualizing of the combined representation is repeated at a third repetition rate greater than the second repetition rate.

13. The method according to claim 12 wherein the third repetition rate is equal to or less than the first repetition rate.

14. The method according to claim 1 further comprising identifying objects located within the first volume based on an analysis of the OCT data from the voxels of the first volume.

15. The method according to claim 14 further comprising enhancing a visibility of selected ones of the identified objects.

16. The method according to claim 15 wherein the enhancing of the visibility comprises displaying a first selected object with a first color and displaying a second selected object different from the first selected object with a second color different from the first color.

17. The method according to claim 15 wherein the enhancing of the visibility comprises displaying a surface of the selected identified objects.

18. The method according to claim 15 wherein the enhancing of the visibility comprises suppressing displaying of a portion of a representation of the OCT data of the first set of voxels, which is unrelated to the selected identified objects.

19. The method according to claim 14 further comprising determining a distance between one of the identified objects and the movable instrument.

20. The method according to claim 19 further comprising generating a signal if the determined distance is less than a predetermined threshold.

21. The method according to claim 14 wherein the identified objects comprise an epiretinal membrane.

22. The method according to claim 1 further comprising visualizing a combined representation of the OCT data of the first set of voxels and of data representing the movable instrument.

23. The method according to claim 22 further comprising generating the data representing the movable instrument based on at least one of the position data indicative of the position of the predetermined portion of the movable instrument and predetermined geometrical data representing a shape of the movable instrument.

24. An optical system including an OCT system, wherein the optical system is operable to visualize objects and configured to obtain OCT data from voxels within a first volume having a first lateral extent, the optical system comprising:
a position measurement unit operable to obtain position data indicative of a position of a predetermined portion of a movable instrument relative to the optical system;
a voxel determination unit operable to determine a first set of voxels from the voxels of the first volume based on the determined position such that at least 80% of the first set of voxels is located within a second volume, the second volume having a second lateral extent, wherein the second lateral extent has a size which is at least 2 times smaller than a size of the first lateral extent;
a data collection unit operable to obtain OCT data of the first set of voxels;
a visualization unit operable to visualize a representation of the OCT data of the first set of voxels; and
a control system operable to repeat the obtaining of the position data, the determining of the first set of voxels, the obtaining of the OCT data of the first set of voxels and the visualizing of the representation at a first repetition rate higher than 5 times per second.

25. The optical system according to claim 24 further comprising a display, wherein the optical system is configured to visualize the representation of the OCT data of the first set of voxels via the display.

26. The optical system according to claim 25 wherein the display comprises at least one of a pair of oculars, a head mounted display, a Boom system and a 3D monitor.

27. The optical system according to claim 24 wherein the movable instrument includes forceps.

28. The optical system according to claim 24 wherein the movable instrument comprises at least one reflecting component.

* * * * *